| United States Patent [19] | [11] | 4,263,221 |
|---|---|---|
| Schnabel et al. | [45] | Apr. 21, 1981 |

[54] PROCESS FOR THE PREPARATION OF AROMATIC CARBODIIMIDES

[75] Inventors: Wilhelm J. Schnabel, Branford; Robert M. Early, North Branford, both of Conn.

[73] Assignee: Olin Corporation, New Haven, Conn.

[21] Appl. No.: 143,074

[22] Filed: Apr. 24, 1980

[51] Int. Cl.$^3$ .......................................... C07C 119/055
[52] U.S. Cl. ...................... 260/453 AM; 260/453 AR
[58] Field of Search ................. 260/453 AR, 551 CD, 260/453 AM

[56] References Cited

U.S. PATENT DOCUMENTS

| 2,757,184 | 7/1956 | Pelley ............................ 260/453 AR |
| 2,853,473 | 9/1958 | Campbell et a. .......... 260/453 AR X |
| 3,157,662 | 11/1964 | Smeltz ...................... 260/551 CD X |

OTHER PUBLICATIONS

Gavin et al., J. Org. Chem., vol. 32, 2511 (1967).
Nurzer et al., Chemical Reviews, vol. 67, No. 2, pp. 107-152, (1967).

*Primary Examiner*—Dolph H. Torrence
*Attorney, Agent, or Firm*—William D. Sabo

[57] ABSTRACT

A process for preparing select symmetrical, aromatic carbodiimides by reacting select symmetrical, aromatic ureas with phosgene in an inert liquid reaction medium. The aromatic carbodiimides produced are useful as components in the preparation of cellular and noncellular polyurethanes, and they can also be used as components in the preparation of isocyanate compositions.

8 Claims, No Drawings

PROCESS FOR THE PREPARATION OF AROMATIC CARBODIIMIDES

This invention relates to a process for the preparation of select aromatic carbodiimides, and, more particularly, to a process for preparing select aromatic carbodiimides by reacting phosgene with select aromatic ureas in an inert liquid reaction medium.

Aromatic carbodiimides can be prepared by heating isocyanates in the presence of catalysts. The patent issued to Smeltz, U.S. Pat. No. 3,157,662 on Nov. 17, 1964, discloses the use of organo-metallic catalysts; and U.S. Pat. No. 2,853,473, issued to Campbell et al on Sept. 23, 1953, discloses the use of phospholine and phospholidene catalysts. The use of both of these types of catalysts is not entirely satisfactory, however, because the reactions which involve the use of them are difficult to control. It is difficult, if not impossible, to remove these catalysts during the course of the reactions; and this problem results in products which are unstable and in the formation of undesirable high molecular weight materials.

To avoid the problems associated with these catalytic reactions, aromatic carbodiimides can also be produced by heating isocyanates without the addition of catalysts. However, when no catalyst is employed, relatively high temperatures, generally 220° C. and higher, and relatively long reaction times, about 16 hours or more, are required in order to obtain even low yields of carbodiimides. Furthermore, this procedure also produces undesirable by-products, such as, for example, isocyanurates.

There is a need at the present time for a process for preparing aromatic carbodiimides which can be more readily controlled to avoid the problems encountered with the catalytic reactions of the prior art.

It is a primary object of the present invention to provide an improved process for the preparation of aromatic carbodiimides.

It is another object of this invention to provide a process for the preparation of select aromatic carbodiimides which produces symmetrical, aromatic carbodiimides having terminal -NCO groups and which are stable and have well-defined low molecular weights.

It is still a further object of this invention to provide a process for the preparation of select aromatic carbodiimides requiring relatively moderate temperatures and relatively short reaction times, and in which the aromatic carbodiimides are obtained in satisfactory yields and without the formation of significant quantities of undesired high molecular weight materials.

These and other objects of the invention will be apparent from the following detailed description thereof.

It has now been discovered that symmetrical, aromatic carbodiimides can be produced in satisfactory yields and under relatively mild and controllable reaction conditions by reacting a symmetrical, aromatic urea with phosgene in an inert liquid reaction medium.

The symmetrical, aromatic ureas which are useful in the process of the present invention are compounds represented by the following formulas:

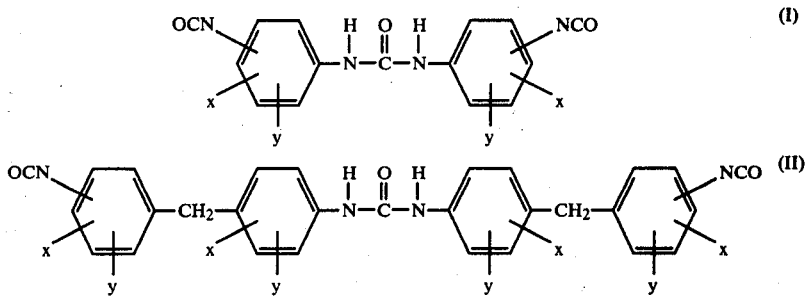

wherein x is hydrogen, alkyl, or halogen and y is hydrogen, alkyl, alkoxy, alkylaryl, or halogen.

Typical examples of symmetrical, aromatic ureas suitable for use as a reactant in the process of this invention and represented by Formula I are the following:
Bis(3-isocyanato-4-methylphenyl)urea
Bis(3-isocyanato-2-methylphenyl)urea
Bis(3-isocyanato-4-ethylphenyl)urea
Bis(3-isocyanato-2-ethylphenyl)urea
Bis(3-isocyanato-4-methyl-6-chlorophenyl)urea
Bis(3-isocyanato-2methyl-5-chlorophenyl)urea
Bis(3-isocyanato-4-methyl-5-bromophenyl)urea
Bis(3-isocyanato-2-methyl-5-bromophenyl)urea
Bis(3-isocyanato-4-chlorophenyl)urea
Bis(3-isocyanato-4-methoxyphenyl)urea.

Specific examples of suitable symmetrical, aromatic ureas which can be used as reactants and represented by Formula II are the following ureas:
Bis 4-(4-isocyanatobenzyl)-phenyl urea
Bis 4-(2-isocyanatobenzyl)-phenyl urea
Bis 2-(2-isocyanatobenzyl)-phenyl urea
Bis 4-(4-isocyanato-3-chlorobenzyl)-2-chlorophenyl urea
Bis 4-(4-isocyanato-3-methylbenzyl)-2-methylphenyl urea.

However, preferred embodiments employ as reactants in the process of this invention the following symmetrical, aromatic ureas:
Bis(3-isocyanato-4-methylphenyl)urea and
Bis 4-(4-isocyanatobenzyl)-phenyl urea The above urea compounds of Formula I or II are for the most part well known in the art and can be prepared by conventional procedures which will be obvious to those skilled in the art. For example, a process for preparing such ureas is disclosed in U.S. Pat. No. 2,757,184, issued to Pelley on July 31, 1956.

According to one embodiment of this invention, a symmetrical, aromatic urea represented by Formula I is reacted with phosgene in an inert liquid reaction medium to provide a symmetrical, aromatic carbodiimide in accordance with the following equation:

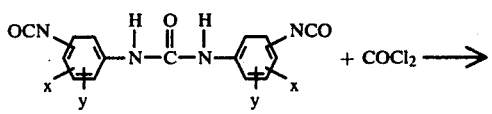

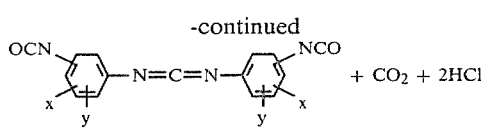

$+ CO_2 + 2HCl$

In another embodiment of this invention, a symmetrical, aromatic urea represented by Formula II is reacted with phosgene in an inert liquid reaction medium to provide a symmetrical, aromatic carbodiimide in accordance with the following equation:

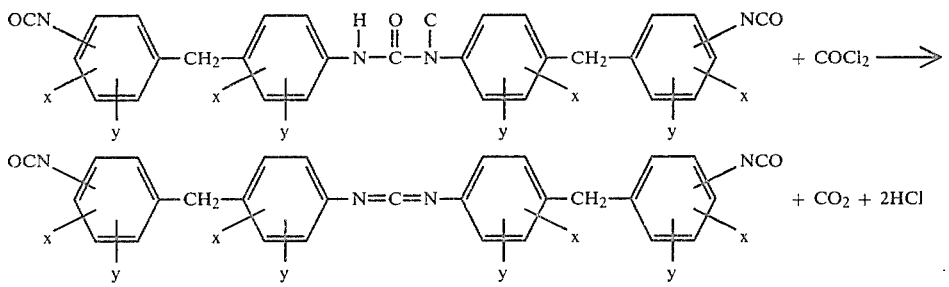

The reactions can be easily controlled and are carried out until phosgenation is complete. The desired symmetrical, aromatic carbodiimides are produced in satisfactory yield, together with isocyanates which may be later removed by distillation, with only trace amounts of high molecular weight materials. Or, the mixture of carbodiimides and isocyanates may be used as such for various applications, for example, in preparing coatings and other noncellular urethanes. It is a discovery of the present invention that at a temperature within the range of about 120° C. to about 150° C., the formation of aromatic carbodiimides in the resulting mixture predominates. On the other hand, as the temperature is increased above about 150° C., the product generally includes a greater proportion of isocyanates than carbodiimides. Below about 120° C., an unacceptable production of undesired insoluble materials occurs. Furthermore, the reaction is characterized by providing aromatic carbodiimides under readily controllable conditions as compared to the reactions using known catalysts, and without the formation of significant quantities of undesired high molecular weight materials.

In converting the symmetrical, aromatic ureas to the corresponding symmetrical, aromatic carbodiimides in accordance with the above equations, the conversion is carried out with phosgene in the presence of an inert liquid reaction medium. Suitable liquid reaction media include any solvents which are chemically inert to the components of the reaction system. Suitable solvents include aliphatic, cycloaliphatic, and aromatic solvents such as n-heptane, cyclohexane, benzene, toluene, and xylene, and halogenated aliphatic and aromatic hydrocarbons such as dichloromethane, tetrachloromethane, monochloronaphthalene, monochlorobenzene, orthodichlorobenzene, p-dichlorobenzene, trichlorobenzene, and perchloroethylene, as well as mixtures thereof and the like.

The proportion of solvent is not critical and any proportion may be employed which will not require excessively large equipment to contain. Generally, for example, the weight percent of aromatic urea in the solvent is in the range between about 2.0 and about 75 percent, but greater or lesser proportions may be employed, if desired.

In carrying out the conversion of the symmetrical, aromatic urea compounds to their corresponding symmetrical, aromatic carbodiimides, the urea compound is typically dissolved in the inert liquid reaction medium and phosgene is added. The phosgene may be introduced either in its liquid or gaseous form, and is preferably used in excess of that needed to react quantitatively with the urea groups. The molar ratio of phosgene:symmetrical, aromatic urea is preferably in the range of from about 1:1 to about 10:1, and most preferably in the range of from about 5:1 to about 10:1 It should be apparent to those skilled in the art that when a stoichiometric excess of phosgene is utilized, the excess of that needed in carrying out the reaction can be recovered, recycled, and reused.

While temperatures of from about 120° C. to about 150° C. can be employed in the process of this invention to obtain a product mixture in which the proportion of carbodiimides predominates over that of isocyanates, preferred embodiments utilize temperatures in the range of from about 120° C. to about 130° C. Pressure is not a critical feature of this invention. However, the reaction is preferably carried out at either atmospheric pressure, or at a pressure slightly elevated over atmospheric pressure.

The reaction time is dependent upon the symmetrical, aromatic urea being reacted, the temperature and the pressure, the amount of phosgene being introduced and the type of equipment utilized. Usually between about ¼ hour and about 1 hour is required to obtain the desired degree of reaction in a batch technique, the most preferred reaction time being within the range of from about ¼ hour to about ½ hour. However, it should be understood that both shorter or longer reaction times may be employed, if desired.

The reaction can be carried out batchwise, semicontinuously, or continuously.

After phosgenation is complete, the reaction mixture is purged with nitrogen to remove excess phosgene and hydrogen chloride formed during the reaction. Typically the mixture is initially purged with nitrogen for about 1½ hour at reaction temperature, and then further purged with nitrogen for about 1 hour at a temperature in excess of the reaction temperature, such as 160° C. However, nitrogen purging for shorter or longer times and at other temperatures may be carried out depending upon the symmetrical, aromatic urea and the molar excess of phosgene employed.

After purging with nitrogen, the inert solvent may be removed by distillation to obtain a mixture of carbodiimide and isocyanate products. If it is desired to isolate the symmetrical, aromatic carbodiimide from the isocyanate, fractional distillation is preferably employed. However, other suitable separation techniques such as extraction, precipitation, etc., may be utilized to separate the symmetrical, aromatic carbodiimide from the isocyanate compound and any byproducts that may be formed.

Although the process of this invention has been described above in connection with the formation of symmetrical, aromatic carbodiimides from substantially pure symmetrical, aromatic ureas, it should be recognized that relatively impure materials containing symmetrical, aromatic ureas can also be reacted in accordance with the process of this invention to convert symmetrical, aromatic ureas contained therein into symmetrical, aromatic carbodiimides.

Thus, in summary, the process of this invention provides symmetrical, aromatic carbodiimides in satisfactory yield, without the formation of a predominate amount of isocyanates, and with at most only trace amounts of high molecular weight materials. Furthermore, the reactions are readily controlled, and the use of expensive catalysts is avoided. The process produces symmetrical, aromatic carbodiimides which are stable and which have well-defined low molecular weights. In addition to being easily controlled, the reaction also provides the advantages of requiring only moderate temperatures and relatively short reaction times.

The products obtained by practicing the process of this invention have a wide variety of useful applications. For example, the symmetrical, aromatic carbodiimides produced are useful as components in preparing polyurethanes and in preparing isocyanate compositions.

The following examples will serve to illustrate the preparation of select symmetrical aromatic carbodiimides in accordance with the process of this invention.

EXAMPLE I

A 250 ml 3-necked flask equipped with a thermometer, a reflux condenser, a blade stirrer and a gas inlet tube, was charged with 20 grams of N,N'-Bis(3-isocyanato-4-methylphenyl)urea and 180 grams of ortho-dichlorobenzene. The mixture was heated with stirring at a temperature of 130° C., and phosgene was bubbled in at the rate of 1.3 mole/hour for 20 minutes. The mixture was then purged with nitrogen at 160° C. to remove excess phosgene and hydrogen chloride formed during the reaction. Analysis by infrared spectroscopy, liquid chromatography and gas chromatography showed that a mixture containing approximately 50 percent Bis(3-isocyanato-4-methylphenyl) carbodiimide was obtained. No starting material and only traces of higher molecular weight products were detected.

EXAMPLES II-VI

Following the procedure of Example I, a 3-necked flask equipped as in Example I, was charged with 6.0 grams of Bis(3-isocyanato-4-methylphenyl)urea and 594 grams of ortho-dichlorobenzene. The mixture was heated with stirring at a temperature within the range from 120° C. to 170° C. as tabulated below, and phosgene was introduced at the rate of 1.2 grams per minute for 15 minutes. The mixture was then purged with nitrogen at the reaction temperature for ½ hour and then at 160° C. for 1 hour to remove excess phosgene and hydrogen chloride formed during the reaction. Analysis by infrared spectroscopy and gas chromatography showed the following proportions of 2,4-toluene diisocyanate and Bis(3-isocyanato-4-methylphenyl) carbodiimide:

| Example | Reaction Temperature (°C.) | % 2,4-Toluene Diisocyanate | Bis(3-Isocyanato-4-Methylphenyl Carbodiimide |
|---|---|---|---|
| II | 120 | 39.1 | 60.9 |
| III | 130 | 43.8 | 56.2 |
| IV | 145 | 51.5 | 48.5 |
| V | 160 | 68.5 | 31.5 |
| VI | 170 | 70.5 | 29.5 |

What is claimed is:

1. A process for preparing symmetrical, aromatic carbodiimides comprising the step of reacting a symmetrical, aromatic urea with phosgene in an inert liquid reaction medium, said aromatic urea being selected from the group consisting of ureas having the formula

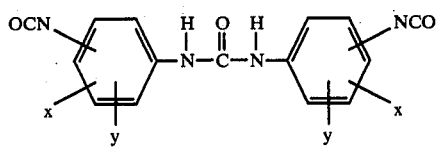

and ureas having the formula

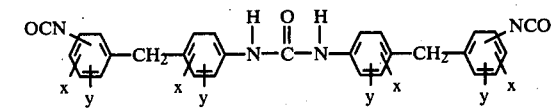

wherein x is selected from the group consisting of hydrogen, alkyl, and halogen and y is selected from the group consisting of hydrogen, alkyl, alkoxy, alkyl-aryl and halogen.

2. The process as recited in claim 1, wherein said aromatic urea is selected from the group consisting of Bis(3-isocyanato-4-methylphenyl)urea and Bis 4-(4-isocyanatobenzyl)-phenyl urea.

3. The process as recited in claim 1, wherein said inert liquid reaction medium is selected from the group consisting of n-heptane, cyclohexane, benzene, toluene, xylene, dichloromethane, tetrachloroethane, monochloronaphthalene, monochlorobenzene, ortho-dichlorobenzene, p-dichlorobenzene, trichlorobenzene, and perchloroethylene.

4. The process as recited in claim 1, wherein the reaction is carried out at a temperature of from about 120° C. to about 150° C.

5. The process as recited in claim 4, wherein the molar ratio of phosgene:aromatic urea is from about 1:1 to about 10:1.

6. The process as recited in claim 5, wherein the reaction is carried out at a temperature of from about 120° C. to about 130° C.

7. The process as recited in claim 6, wherein said aromatic urea is selected from the group consisting of Bis(3-isocyanato-4-methylphenyl) urea and Bis 4-(4-isocyanatobenzyl)-phenyl urea.

8. The process as recited in claim 7, wherein said inert liquid reaction medium is orthodichlorobenzene.

* * * * *